United States Patent
Hogan et al.

(10) Patent No.: US 12,116,578 B2
(45) Date of Patent: Oct. 15, 2024

(54) METHODS AND SYSTEMS OF PCR-BASED RECOMBINANT ADENO-ASSOCIATED VIRUS MANUFACTURE

(71) Applicant: APDN (B.V.I.) Inc., Tortola (VG)

(72) Inventors: Michael E. Hogan, Stony Brook, NY (US); Stephen Hughes, Port Jefferson Station, NY (US); Yuhua Sun, Stony Brook, NY (US)

(73) Assignee: APDN (B.V.1.) 1nc., Tortola (VG)

( * ) Notice: Subject to any disclaimer, the term of this patent is extended or adjusted under 35 U.S.C. 154(b) by 735 days.

(21) Appl. No.: 16/988,025

(22) Filed: Aug. 7, 2020

(65) Prior Publication Data

US 2021/0054384 A1   Feb. 25, 2021

Related U.S. Application Data

(60) Provisional application No. 62/916,333, filed on Oct. 17, 2019, provisional application No. 62/883,701, filed on Aug. 7, 2019.

(51) Int. Cl.
    *C12N 15/70*    (2006.01)
    *C12N 7/00*     (2006.01)
    *C12Q 1/686*    (2018.01)

(52) U.S. Cl.
    CPC .............. *C12N 15/70* (2013.01); *C12N 7/00* (2013.01); *C12Q 1/686* (2013.01); *C12N 2750/14143* (2013.01); *C12N 2750/14151* (2013.01)

(58) Field of Classification Search
    CPC ...................... C12Q 1/686; C12N 2750/14143
    See application file for complete search history.

(56) References Cited

U.S. PATENT DOCUMENTS

| | | | |
|---|---|---|---|
| 7,446,190 B2 | 11/2008 | Sadelain et al. | |
| 7,547,551 B2 | 6/2009 | Schuler et al. | |
| 2011/0081686 A1 | 4/2011 | Manthorpe et al. | |
| 2013/0203634 A1 | 8/2013 | Jovanovick et al. | |
| 2014/0236070 A1 | 8/2014 | Broderick et al. | |
| 2015/0322418 A1 | 11/2015 | Kapoor et al. | |
| 2017/0224798 A1 | 8/2017 | Cooper et al. | |
| 2017/0247756 A1 | 8/2017 | Schreiber et al. | |

FOREIGN PATENT DOCUMENTS

| WO | WO03023000 | 3/2003 |
|---|---|---|
| WO | WO2008127450 | 10/2008 |
| WO | WO2013092723 | 6/2013 |

OTHER PUBLICATIONS

Lee K, Kim YG, Jo EC. Shuttle PCR-based cloning of the infectious adeno-associated virus type 5 genome. J Virol Methods. Aug. 2003;111(2):75-84. doi: 10.1016/s0166-0934(03)00135-6. (Year: 2003).*
Jensen MA, Fukushima M, Davis RW. DMSO and betaine greatly improve amplification of GC-rich constructs in de novo synthesis. PLoS One. Jun. 11, 2010;5(6):e11024. doi: 10.1371/journal.pone.0011024. (Year: 2010).*
Aurnhammer C et al. Universal real-time PCR for the detection and quantification of adeno-associated virus serotype 2-derived inverted terminal repeat sequences. Hum Gene Ther Methods. Feb. 2012;23(1):18-28. (Year: 2012).*
Mroske C, Rivera H, Ul-Hasan T, Chatterjee S, Wong KK. A capillary electrophoresis sequencing method for the identification of mutations in the inverted terminal repeats of adeno-associated virus. Hum Gene Ther Methods. Apr. 2012;23(2):128-36. (Year: 2012).*
Henke W, Herdel K, Jung K, Schnorr D, Loening SA. Betaine improves the PCR amplification of GC-rich DNA sequences. Nucleic Acids Res. Oct. 1, 1997;25(19):3957-8. (Year: 1997).*
Jensen MA, Fukushima M, Davis RW. DMSO and betaine greatly improve amplification of GC-rich constructs in de novo synthesis. PLoS One. Jun. 11, 2010;5(6):e11024. (Year: 2010).*
Lee K, Kim YG, Jo EC. Shuttle PCR-based cloning of the infectious adeno-associated virus type 5 genome. J Virol Methods. Aug. 2003;111(2):75-84. (Year: 2003).*
Saveliev A, Liu J, Li M, Hirata L, Latshaw C, Zhang J, Wilson JM. Accurate and Rapid Sequence Analysis of Adeno-Associated Virus Plasmids by Illumina Next-Generation Sequencing. Hum Gene Ther Methods. Oct. 2018;29(5):201-211. (Year: 2018).*
Ge et al., Genome-wide Gene Deletions in *Streptococcus sanguinis* by High Throughput PCR, Journal of Visualized Experiments, Nov. 2012, vol. 69 e4356, pp. 1-6.
Roth et al., Reprogramming Human T Cell Function and Specificity with Nonviral Genome Targeting, Nature, Jul. 2018, vol. 559, No. 7714, pp. 405-409.
Peters et al., Regulation of Majority Histocompatibility Complex Class I Moecule Expression on Cancer Cells by Amyloid Precursor-Like Protein 2, Immunologic Research, Oct. 2011, vol. 51, 1, pp. 39-44.
Rachlin et al., MuPlex-Objective Multiplex PCR Assay Design, Nucelic Acids Research, Feb. 14, 2005, vol. 33, pp. 544-547.
Lufino et al., Review Advanced in High-capacity Extrachormosomal Vector Technology: Episomal Maintenance, Vector Deliver, and Transgene Expression; Moecular Therapy, 2008, vol. 16, No. 9, pp. 1525-1538.

(Continued)

*Primary Examiner* — Nicole Kinsey White
*Assistant Examiner* — Ruixue Wang
(74) *Attorney, Agent, or Firm* — Hoffmann & Baron, LLP

(57) ABSTRACT

The present invention relates to systems and methods to produce recombinant adeno-associated virus (rAAV) utilizing one or more DNA constructs manufactured via polymerase chain reaction (PCR).

12 Claims, 8 Drawing Sheets
Specification includes a Sequence Listing.

(56) References Cited

OTHER PUBLICATIONS

Wade-Martins et al., An Infectious Transfer and Expression System for Genomic DNA Loci in Human and Mouse Cells, Nature Biotechnology, 2001, vol. 19, pp. 1067-1070.
Annoni et al., Modulation of Immune Responses in Lentiviral Vector-Mediated Gene Transfer, Cellular Immunology, 2018, pp. 1-8.
Bushely et al., A Therapeutic Antibody for Cancer, Derived from Single Human B Cells, Cell Reports, 15, 2016, pp. 1505-1513.
Monjezi et al., Enhanced CAR T-Cell Engineering Using Non-Viral Sleeping Beauty Transposition from Minicircle Vectors, Leukemia, 2017, vol. 31, pp. 186-194.
Labant, Mary, Non-Viral, Plasmid-Free CAR T-Manufacturing Platform Begins Preclinicals, Genetic Engineering and Biotechnology News, 2018, https://www.genenews.com/non-viral-plasmid-free-car-t-manufacturing-platform-begins-preclinicals/.

\* cited by examiner

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cttttgctgg ccttttgctc acatgtcctg c                              31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtaaggagaa aataccgcat caggcgcccc                                30

<210> SEQ ID NO 3
```

```
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcctggcctt ttgctggcct tttgctcaca tgtcctg                              37

<210> SEQ ID NO 4
<211> LENGTH: 145
<212> TYPE: DNA
<213> ORGANISM: Unknown
<220> FEATURE:
<223> OTHER INFORMATION: Description of Unknown:
      ITR sequence

<400> SEQUENCE: 4
aggaacccct agtgatggag ttggccactc cctctctgcg cgctcgctcg ctcactgagg      60
ccgcccgggc aaagcccggg cgtcgggcga cctttggtcg cccggcctca gtgagcgagc     120
gagcgcgcag agagggagtg gccaa                                           145
```

METHODS AND SYSTEMS OF PCR-BASED RECOMBINANT ADENO-ASSOCIATED VIRUS MANUFACTURE

CROSS REFERENCE TO RELATED APPLICATIONS

The present application claims the benefit of U.S. provisional patent application No. 62/883,701 filed on Aug. 7, 2019 and U.S. provisional patent application No. 62/916,333 filed on Oct. 17, 2019, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 1, 2020, is named 189542_SL.txt and is 1,379 bytes in size.

BACKGROUND OF THE INVENTION

1. Technical Field

The present invention relates to systems and methods to produce recombinant adeno-associated virus (rAAV) utilizing one or more DNA constructs manufactured via polymerase chain reaction (PCR).

2. Background of the Invention

The manufacture of large quantities of high-quality DNA is currently a major bottleneck in the production of viral vectors utilized in, among other things, gene therapy and vaccines. Currently, bacterial plasmids, which are small circular episomal DNA molecules that can replicate independently of bacterial chromosomal DNA, are utilized as the primary source of DNA to produce viral vectors. In addition to long amplification times, measured in days or weeks, the amplification of DNA via bacterial plasmids for use in viral vector manufacture has additional drawbacks such as the necessity of complex and expensive purification steps, the risk of endotoxin contamination, antibiotic resistance gene transfer, other plasmid derived DNA sequence transfers, as well as challenges with integration into robotic and/or automated workflows. Moreover, certain DNA sequences that are necessary to produce specific viral vectors (e.g. inverted tandem repeats) are ill-suited for plasmid-based amplification and lead to high failure rates and low viral titer.

One of the most promising viral vectors is adeno-associated virus (AAV), which, in most instances, is manufactured by triple transfection of plasmid DNA constructs into packaging cell lines to produce recombinant adeno-associated virus (rAAV). rAAV manufacture requires three different DNA constructs that must be transfected into a packaging cell line. These DNA constructs are: (i) a DNA construct containing the AAV Rep and Cap genes required for capsid formation and replication ("rep/cap"); (ii) a DNA construct containing the necessary adenovirus helper genes ("AAV helper"); and (iii) a DNA construct containing the cargo (transgene) of interest flanked on both sides by inverted terminal repeats (ITRs) ("[ITR-cargo-ITR]"). These three DNA constructs are currently amplified and supplied to rAAV manufacturing facilities in the form of DNA plasmids.

The ITR DNA sequence of AAV has emerged as an enabling element for rAAV based therapeutics, as any transgene which is to be delivered by a rAAV therapy must be flanked on each side by a single copy of the 145 bp long ITR sequence. Direct proximity of the cargo of interest to the ITR regions is an absolute requirement for successful manufacture of rAAV based therapies, as the ITR regions must be present for successful packaging of the transgene into the viral capsid. Without proper flanking ITR sequences, rAAV will not package the desired transgene (cargo) and the resultant rAAV therapy will fail.

Until now, the three DNA constructs necessary for rAAV production have been manufactured via bacterial plasmid-based systems. Recently, due to concerns about bacterial plasmid safety in therapeutics and the operational challenges created by the use of plasmid-based DNA amplification systems, it has become important to eliminate the use of bacterial plasmids to produce one or more of the DNA constructs necessary to manufacture rAAV. Heretofore, it was believed in the art that scalable and accurate PCR-based amplification of the [ITR-cargo-ITR] construct was not possible due to the unique secondary structures of the ITR regions that are ill suited for PCR-based amplification.

In addition, for certain therapeutic applications, rAAV vectors consisting exclusively or predominantly of single stranded DNA (ssDNA) of a single polarity can lead to higher viral titers and greater efficacy of a resultant therapeutic. ssDNA of a single polarity may be the positive (sense) or reverse/minus (anti-sense) polarity of the rAAV ssDNA genome. Herein, systems and methods of creating single polarity rAAV vectors produced via PCR-based manufacturing of specialized [ITR-cargo-ITR] amplicons are disclosed.

The invention of the instant application discloses novel methods and systems for the PCR-based manufacture of the DNA constructs necessary for rAAV production, including the [ITR-cargo-ITR] construct. In addition, the methods and systems of the instant application can also be adopted to produce rAAV vectors packing a single polarity of its ssDNA genome via the use of specialized [ITR-cargo-ITR] amplicons.

BRIEF SUMMARY OF THE INVENTION

The present invention relates to systems and methods to produce recombinant adeno-associated virus (rAAV) utilizing one or more DNA constructs produced via polymerase chain reaction (PCR).

In one aspect, the invention provides a method for amplifying a DNA sequence comprising the general sequence structure of [ITR-cargo-ITR] wherein: (i) the 3' terminus of both the forward and reverse PCR primer pair is designed to overlap only the last 2-8 bases of the "A" ITR sequence; (ii) the 5' end of each PCR primer extends into about 20-35 bases of the flanking DNA sequence adjacent to the ITR sequences; (iii) the PCR cycling parameters have a combined annealing/extension step at a temperature greater than 70° C.; and (iv) the PCR master mix contains one or more osmolytes. In some embodiments, the osmolyte may be betaine. In another aspect, the DNA flanking sequences are designed for high-affinity PCR primer binding.

In another aspect, a method of manufacturing amplicon polynucleotides containing the sequence motif [ITR-cargo-ITR] via CPR is provided, said method comprising: (i) obtaining a desired template DNA sequence containing a [ITR-cargo-ITR] DNA sequence motif; (ii) designing a PCR primer pair such that the 3' terminus of both the forward and reverse PCR primers overlap only about the last 2-8 bases of the A and A' ITR sequences and the 5' terminus of both the forward and reverse PCR primers extend into about 20-35 bases of the flanking DNA sequences adjacent to the ITR sequences; (iii) performing a PCR amplification reaction with PCR cycling parameters comprising a combined annealing/extension step at a temperature greater than 70° C., wherein the PCR amplification reaction contains on or more osmolytes, thereby producing a plurality of amplicon polynucleotides containing the desired DNA sequence motif [ITR-cargo-ITR]. In preferred embodiments, the osmolyte is betaine. The template DNA sequence containing a [ITR-cargo-ITR] DNA sequence motif may be obtained from a plasmid or from a non-plasmid source such as a DNA construct assembled with solid-state syntheses or other polynucleotide manufacturing process. The resultant plurality of amplicon polynucleotides containing the desired DNA sequence motif [ITR-cargo-ITR] may or may not be sequence verified via next generation sequencing. A representative sample of the amplicon polynucleotides containing the desired DNA sequence motif [ITR-cargo-ITR] may also be verified via next generation sequencing.

In another aspect, a method for the production of recombinant adeno-associated virus (rAAV) is disclosed, said method comprising: (i) obtaining a desired template DNA sequence containing a [ITR-cargo-ITR] DNA sequence motif; (ii) designing a PCR primer pair such that the 3' terminus of both the forward and reverse PCR primers overlap only about the last 2-8 bases of the A and A' ITR sequences and the 5' terminus of both the forward and reverse PCR primers extend into about 20-35 bases of the flanking DNA sequences adjacent to the ITR sequences; (iii) performing a PCR amplification reaction with PCR cycling parameters comprising a combined annealing/extension step at a temperature greater than 70° C., wherein the PCR amplification reaction contains on or more osmolytes, thereby producing a plurality of amplicon polynucleotides containing the desired sequence motif [ITR-cargo-ITR]; (iv) obtaining a quantity of the AAV rep/cap DNA sequence; (v) obtaining a quantity of AAV helper DNA sequence; (vi) transfecting the amplicon polynucleotides containing the desired sequence motif [ITR-cargo-ITR], the AAV rep/cap DNA sequence and the AAV helper DNA sequence into a packaging cell line; (vii) after cell line expansion, lysing and purifying the lysed cells to collect a quantity of rAAV.

In yet another aspect, through use of forced asymmetrical PCR or ITR modification, rAAV vectors packaging a single polarity of its ssDNA genome can be manufactured via the use of specialized [ITR-cargo-ITR] amplicon polynucleotides.

BRIEF DESCRIPTION OF THE FIGURES

The accompanying drawings, which are incorporated into and form a part of the specification, illustrate one or more embodiments of the present invention and, together with the description, serve to explain the principles of the invention. The drawings are only for the purpose of illustrating the preferred embodiments of the invention and are not to be construed as limiting the invention. In the drawings.

DETAILED DESCRIPTION OF THE INVENTION

Figure 1:
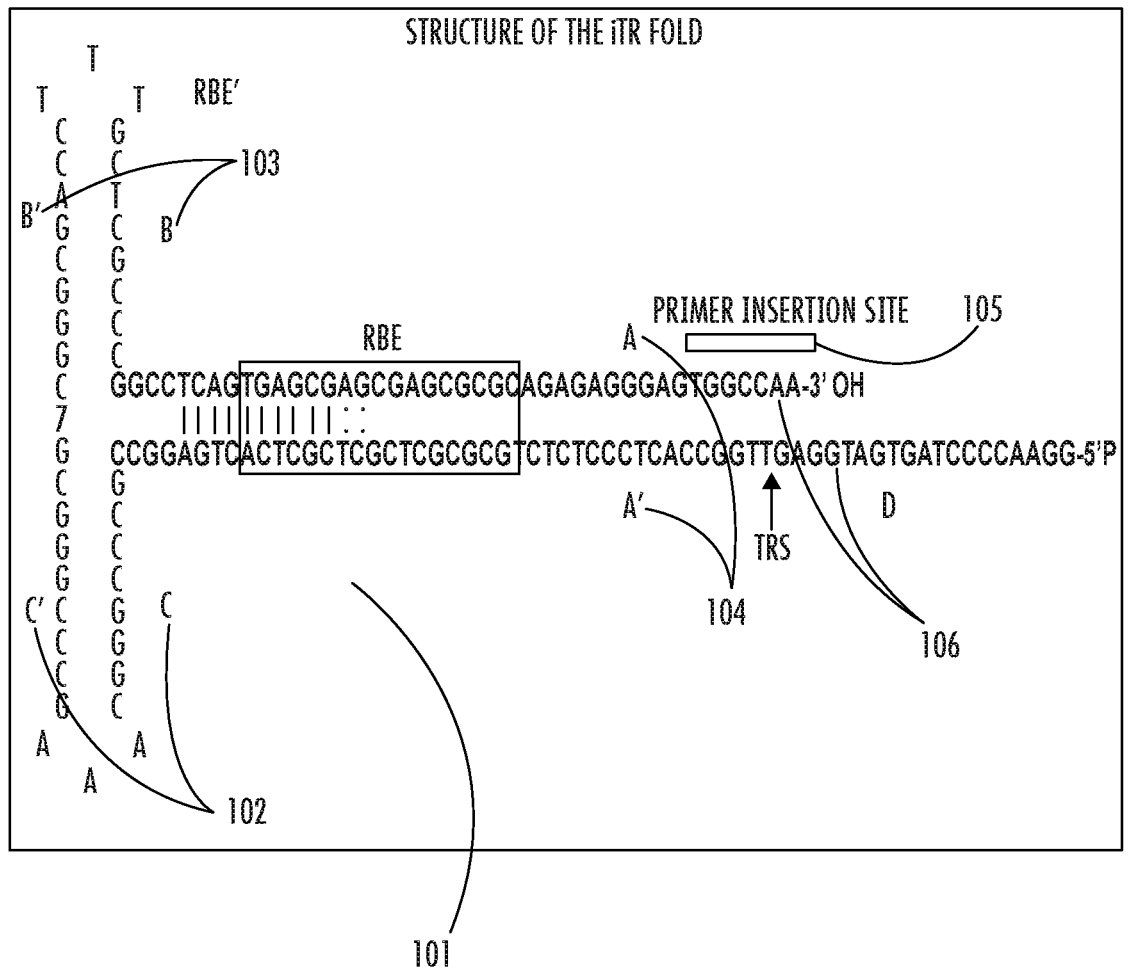
FIG. 1 is a wild-type ITR DNA sequence (SEQ ID NO: 4) showing the ITR secondary structure, the A, B, C and D elements, and the location of primer binding according to an embodiment of the invention.

The following documentation provides a detailed description of exemplary embodiments of the invention. Although a detailed description as provided herein contains many specifics for the purposes of illustration, anyone of ordinary skill in the art will appreciate that many variations, equivalents and alterations to the following details are within the scope of the invention. Accordingly, the following preferred embodiments of the invention are set forth without any loss of generality to, and without imposing limitations upon, the claimed invention. Thus, the scope of the invention should be determined by the appended claims and their legal equivalents, and not merely by the preferred examples or embodiments given herein.

Definitions

The term "amplicon" as used herein means a DNA or RNA polynucleotide that is the product of an enzymatic or chemical based amplification event or reaction. Amplification events or reactions include, without limitation, the polymerase chain reaction (PCR), loop mediated isothermal amplification, rolling circle amplification, nucleic acid sequence base amplification, and ligase chain reaction or recombinase polymerase amplification. An amplicon may be comprised of single stranded and/or double stranded DNA, and/or a combination thereof. An amplicon cannot be produced by or be the product of bacterial plasmid propagation within bacteria.

The term "continuous flow PCR device" means a PCR device as disclosed in U.S. Pat. Nos. 8,293,471, 8,986,982 and 8,163,489.

The term "episomal" means a DNA polynucleotide that replicates independently from chromosomal DNA. Episomal DNA may reside in a cell's nucleus.

The term "expression" refers to the transcription and/or translation of an expression cassette.

The term "expression cassette" means a nucleic acid sequence consisting of one or more genes and the sequences controlling their expression. At a minimum, an expression cassette shall include a promoter (or other expression control sequence) and an open reading frame (ORF).

The term "expression control sequence" means a nucleic acid sequence that directs transcription of a nucleic acid and/or open reading frame. An expression control sequence can be a promotor or an enhancer.

The term a "subject" is any mammal, including without limitation humans, monkeys, farm animals, pets, horses, dogs and cats. In an exemplary embodiment, the subject is human.

The term "next generation sequencing" (NGS) includes any form of high-throughput DNA or RNA sequencing. This includes, without limitation, sequencing by synthesis, sequencing by ligation, nanopore sequencing, single-molecule real-time sequencing and ion semiconductor sequencing.

The term "transfection" means the uptake of exogenous or heterologous RNA or DNA by a cell. Without limitation, transfection may be accomplished by direct uptake, electroporation, chemical or other substance-based methods (e.g. calcium chloride, rubidium chloride, alcohol, DEAE-dextran, PEI) lipofection, soluporation, cationic liposomes, cationic polymers, lipoplexes, synthetic branched dendrimers, microprojectile bombardment, cellular surgery, lipid nanoparticles (LNPs), and/or viral transduction.

The term "large-scale PCR" means a PCR reaction wherein the total PCR reaction volume is greater than 0.7 liters. Large-scale PCR may be performed in a single reaction vessel or may be performed in a plurality of reaction vessels simultaneously.

The term "cargo" means one or more expression cassettes. Cargo, may be, without limitation, a transgene.

The term "transgene" means a gene, genetic material or other expression cassette that is artificially introduced into the genome of a subject.

The term "ITR" means inverted terminal repeat DNA sequence. The ITR sequence may be wild-type and comprise 145 bases each. The ITR sequence may also be modified and may be comprised of more or less than 145 bases. The ITR may be comprised of wild-type A, B, C and D elements, or one or more of said elements may be modified.

The term "[ITR-cargo-ITR]" means a DNA sequence comprised of the general motif of a cargo (transgene) flanked on both sides by an ITR sequence. A [ITR-cargo-ITR] is flanked on either side by a flanking sequence.

The use of the alternative (e.g., "or") should be understood to mean either one, both, or any combination thereof of the alternatives. As used herein, the indefinite articles "a" or "an" should be understood to refer to "one or more" of any recited or enumerated component.

PCR Amplification of the [ITR-Cargo-ITR] DNA Construct

The two ITR sequences that flank the transgene cargo in the important [ITR-cargo-ITR] DNA construct necessary for rAAV manufacture are poorly compatible with ordinary methods of PCR-based production. This poor compatibility stems from the structure of the ITR sequence domain, rather than its proximity to the transgene.

As shown in FIG. 1, the ITR sequence (101) is extremely G-C rich and contains multiple self-complementary sequences A/A' (104) BB' (103) and C/C' (102) that allow the single stranded version of the ITR sequence to fold into a very stable stem-loop secondary structure (101). Both ITR sequences are flanked by flanking sequences (106) that may or may not form secondary structures. These features of the ITR, which are necessary for successful rAAV production, are problematic for conventional PCR-based amplification, which struggles with both G-C rich sequences and secondary structures. Under conventional PCR-based amplification methodologies, upon the first heat denaturation step in the PCR reaction, a dsDNA template containing an ITR region is denatured to form the corresponding ssDNA template, which upon cooling, is driven by the presence of self-complementary G-C rich regions (102, 103 and 104) to fold into the highly stable hairpin secondary structure (101) shown in FIG. 1, which serves to block proper PCR primer (105) binding to the template necessary to initiate PCR amplification and, subsequently, the extension of the bound primer through the highly folded template's secondary structure. The result is: (i) complete failure to amplify the [ITR-cargo-ITR] construct; (ii) very low amplification yield of the [ITR-cargo-ITR] construct; and/or (iii) amplification of the [ITR-cargo-ITR] construct resulting in one or more undesired side reactions producing additional amplicons.

Embodiments of the systems and methods of the present invention address these issues with novel systems and methods for the PCR-based amplification of the [ITR-cargo-ITR]. In an embodiment, a [ITR-cargo-ITR] DNA construct may be successfully amplified via PCR by utilizing the following PCR modifications in conjunction: (i) PCR primers designed for calculated minimal insertion into the ITR fold of between 2 and 10 bases in the area of the A/A' (104); (ii) extension of the 5' end of the PCR primer into about 20 bases to 30 bases of ITR flanking DNA sequence (106) such that the forward and reverse PCR primers bind to the flanking regions with high affinity and with minimal insertion into the ITR fold of between 2 and 10 bases; (iii) use of high annealing temperature based two-step PCR; and (iv) the introduction of an osmolyte into the PCR reaction buffer. The PCR primers may also be designed for calculated minimal insertion into the ITR fold of between 2 and 8 bases; 2 and 6 bases; and 2 and 5 bases.

In an embodiment, a [ITR-cargo-ITR] DNA construct is PCR amplified according to the following method: (i) design and assembly of forward and reverse PCR primers that bind to the ITR flanking regions of a [ITR-cargo-ITR] construct (106), wherein the 3' terminus of said forward and reverse PCR primers minimally insert into the ITR fold between 2 and 8 bases in the area of A/A' (104) when bound to flanking regions and wherein the 5' terminus of said forward and reverse PCR primers extend into about 20-35 bases of the flanking region DNA sequences (106); (ii) the inclusion of betaine or other osmolyte into the PCR reaction composition; and (iii) the utilization of 2-step PCR with a combined annealing/extension temperature greater than 70° C.

Figure 3:
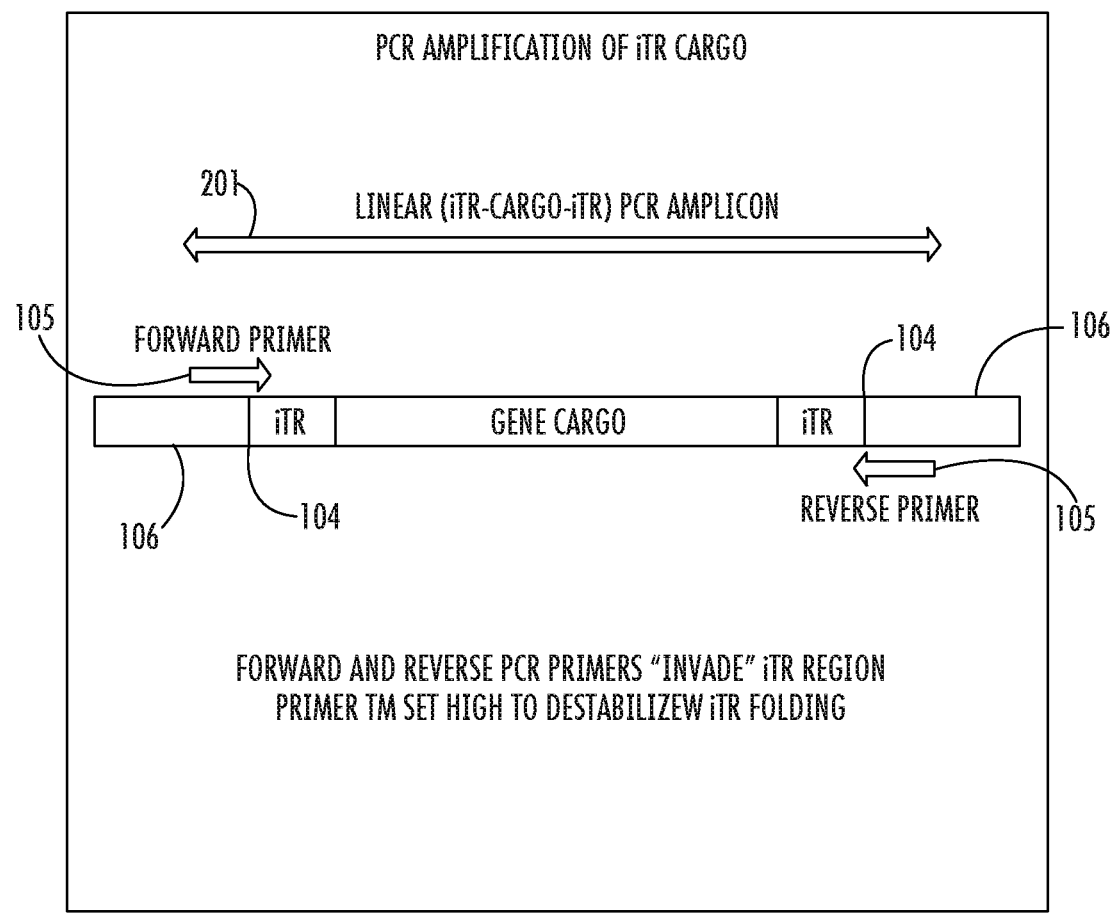
FIG. 3 is an illustration of the primer design principle according to an embodiment of the invention.

The PCR primers according to the subject invention are designed such that the 3' terminus of both the forward and reverse primer pair only minimally invade the ITR sequences. As shown in FIG. 3, in exemplary embodiments, the 3' termini of both the forward (105) and reverse (105) PCR primers are designed to invade and bind to only the last about 2-8 bases of the ITR A/A' stem region (104), thereby inserting the flanking region bound PCR primers (105) into the A/A' stem (104) over a region of only between 2-8 bases. This de minimis insertion into the A/A' stem region (104) serves to destabilize the A/A' stem region and, in turn, the overall structure of the ITR fold to facilitate successful high-fidelity PCR amplification of a [ITR-cargo-ITR] construct to create amplicons comprising the [ITR-cargo-ITR] (201). Experimentation has shown that design of primers that bind to more than approximately 10 bases of the ITR A/A' stem leads to low amplification efficiencies, loss in accurate and/or the amplification of several side products.

In an alternative embodiment, the 3' termini of both the forward and reverse PCR primer pair are designed to only bind to the last between 2 and 5 bases of the ITR A/A' stem region (104).

In general, the [ITR-cargo-ITR] region is embedded in a larger DNA fragment and is thus flanked to either side by DNA flanking sequences (106), i.e. Flank-[ITR-cargo-ITR]-Flank. Having designed the 3' termini of the PCR forward and reverse primers for minimal ITR insertion and binding as described above, the remainder of the PCR forward and reverse primers sequences are designed to bind to between 20-35 bases of the adjacent flanking sequences (106), thus yielding a PCR primer that is 30-40 bases in length and designed to span the junction between the ITR A/A' stem (104) and flanking region DNA sequence (106). The 5' end of the PCR forward and reverse primers are kept long (20-35 bases) to allow for high affinity binding to the flanking region DNA sequence (to drive disruption of the stable ITR fold) and to ensure that forward and reverse primer binding is specific to the target template DNA sequence comprising the Flank-[ITR] junction.

Generally, PCR amplification reactions are performed as a series of three steps at the stated temperatures or within the stated temperature ranges: (i) denaturing step at 98° C.; (ii) annealing step at between 55° C. to 65° C.; and (iii) extension step at between 70° C. to 73° C.

In the present invention, the PCR amplification reaction is reduced to 2 steps, through the creation of a single high temperature annealing and extension step. In an embodiment, 2-step PCR amplification of a [ITR-cargo-ITR] construct is accomplished via the use of a denaturing step at 98° C. and a single combined high temperature annealing and extension step at above 70° C. In an exemplary embodiment, temperatures between 70° C. and 73° C. may be used. This results in high temperature annealing at above 70° C. versus the conventional range of 55° C. to 65° C. for an annealing step. The elimination of the lower temperature annealing in favor of high temperature annealing destabilizes the ITR structure by keeping temperature higher than 70° C. throughout the entire PCR amplification reaction. Without the use of an annealing temperature above 70° C. the secondary structure of the ITR sequence would form during the PCR reaction, thereby greatly diminishing amplification yield and/or fidelity.

Amplification of a [ITR-cargo-ITR] construct is further facilitated via the use of specific PCR enhancers. While the concept of PCR enhancers are well known in the art, including DMSO, PEG, glycerol, BSA, betaine and other osmolytes, the inventor has found that, while most osmolytes tested, such as DMSO, seem not to be effective in supporting PCR amplification of a [ITR-cargo-ITR] construct, the osmolyte betaine significantly increases PCR efficiency and fidelity specifically of a [ITR-cargo-ITR] construct when coupled with the other PCR modifications described herein. Betaine as a PCR enhancer is unique in that the inventor has shown betaine to stabilize DNA polymerases (including Taq Polymerase) against thermal denaturation, while selectively destabilizing the formation of G-C base pairs at elevated temperature due to selective solvation of free guanosine. Thus, the inventors have discovered that the unique polymerase stabilization and G-C base pair destabilization imparted by betaine are required to obtain adequate PCR yields from [ITR-cargo-ITR] constructs without significant side reactions. In an exemplary embodiment, betaine is used at 0.5M concentration in the PCR reaction. In other alternative embodiments, betaine is utilized at between 1M and 0.01M concentrations in the PCR reaction.

The PCR produced [ITR-cargo-ITR] construct may be transfected into packaging cell lines (such as HEK293 or other cell lines known in the art) along with conventional AAV helper and rep/cap plasmids to produce rAAV. The PCR produced [ITR-cargo-ITR] construct may also be transfected into packaging cell lines along with AAV helper and rep/cap constructs, wherein one or both constructs are amplicon polynucleotides manufactured by PCR. The packaging cell lines may be optimized for use with PCR produced [ITR-cargo-ITR] constructs and/or AAV helper and rep/cap constructs wherein one or both are manufactured by PCR. PCR-produced [ITR-cargo-ITR], AAV helper and rep/cap constructs may be produced by large-scale PCR. The large-scale PCR may be continuous flow.

Transfection into packaging cell lines may be accomplished via any methods known in the art. Exemplary methods include, without limitation, direct uptake, electroporation, chemical or other substance-based methods (e.g. calcium chloride, rubidium chloride, alcohol, DEAE-dextran, polyethylenimine (PEI)) lipofection, cationic liposomes, soluporation, lipid nanoparticles (LNP), cationic polymers, lipoplexes, synthetic branched dendrimers, microprojectile bombardment and cellular surgery. Viral transduction or transposon/transposase systems may also be used.

PCR-produced [iTR-cargo-iTR], AAV helper and/or rep/cap constructs may also be manufactured via methods and systems that mitigate PCR-based sequence error. Extremely high-fidelity polymerase such as Q5® polymerase (NEB Biolabs, Inc. USA) with an error rate less than $5.3 \times 10^{-7}$ in the PCR reaction may be used. PCR conditions may also be optimized to increase fidelity. Large-scale PCR can be used in conjunction with high-fidelity polymerase to amplify [ITR-cargo-ITR], AAV helper and/or rep/cap constructs to economically create a high copy number of amplicons for use in rAAV manufacture.

After PCR amplification, the resultant [iTR-cargo-iTR], AAV helper and/or rep/cap construct amplicons may be sequence verified via NGS before transfection into packaging cell lines or a representative sample of the amplicons may be sequenced via NGS as part of quality control. In addition, post transfection, the packaging cell lines (or a representative sample thereof) may undergo RNA sequence analysis via NGS to ascertain whether the transfected cells are expressing the correct RNA sequence based on the desired sequence of the transfected amplicons. Post transfection, viral assembly and lysing of the packing cells, samples of the resultant rAAV may also be sequenced via NGS to confirm sequence accuracy. Samples of the resultant rAAV may also be interrogated via mass spectrometry to ensure correct structure and sequence. In addition, the cargo (transgene) sequence of the resultant rAAV may be specifically interrogated via NGS to ensure proper DNA sequence prior to introduction into a subject.

Production of rAAV Containing Single Polarity ssDNA Utilizing Forced Asymmetric PCR Primer Template Amplification to Produce Single Polarity [ITR-Cargo-ITR] Amplicon.

In an aspect of the invention, specialized [ITR-cargo-ITR] amplicons can also be used to produce single polarity rAAV vectors. While rAAV vectors containing exclusively positive (sense) polarity of ssDNA are set forth in this exemplary embodiment, the method and system disclosed herein can similarly by utilized to manufacture rAAV vectors containing only negative (antisense) polarity of ssDNA.

Figure 4:
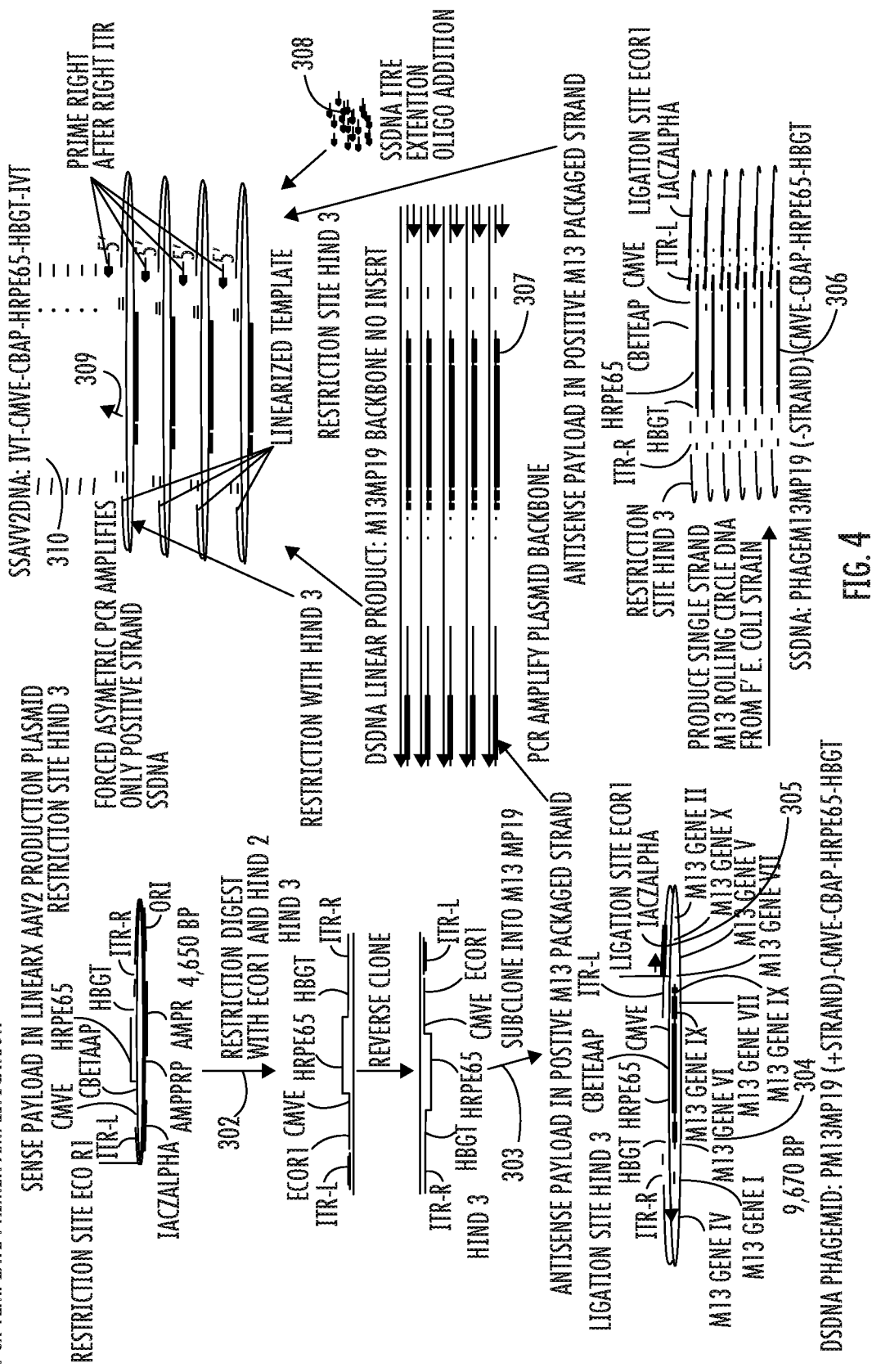
FIG. 4 is a flow diagram of an embodiment of the system and method to manufacture single polarity rAAV vectors via the use of specialized [ITR-cargo-ITR] amplicons.

As shown in FIG. 4, the first step is preparation of the reverse (−) payload plasmid dsDNA PHAGEMID: pM13mp19 (+strand)-CMVe-CBAp-hRPE65-hBGt (301). The starting plasmid is a production plasmid containing the expression cassette for the transgene (cargo) of interest. This double-stranded dsDNA production plasmid, designated p-CMVe-CBAp-hRPE65-hBGt (301), may reside in a pUC18 plasmid or other commercially available cloning vector. This is a positive (sense) strand expression cassette plasmid where positive (sense) refers to the direction the transgene is transcribed from the DNA strand by mRNA from 5' to 3'. Negative (antisense) refers to the reverse direction 3' to 5'.

The cloning plasmid is digested with the restriction enzymes EcoR1 and Hind3 (302) to release and reverse the restricted expression cassette, which is purified and inserted into an M13mp19 plasmid precut with EcoR1 and Hind 3. As shown in FIG. 4, the expression cassette is subcloned in the reverse direction into the multiple cloning site of M13mp19 plasmid or other suitable cloning plasmid so that the negative strand of the expression cassette is placed into M13mp19 or other suitable cloning plasmid (303). After the expression cassette insert is subcloned into M13mp19 or other suitable cloning plasmid (303), it will provide the negative strand for a PCR amplification template. This will allow the negative strand to be used as a template once primed with the positive strand of the PCR amplification of the backbone using PCR primers amplifying the plasmid backbone. The antisense payload (305) in the positive M13mp19 packaged strand has a Hind3 site at the end of the expression vector for use in forced asymmetric PCR. This resulting plasmid is referred to as dsDNA PHAGEMID: pM13mp19 (+strand)-CMVe-CBAp-hRPE65-hBGt (304).

The second step as shown in FIG. 4 is using the dsDNA PHAGEMID: pM13mp19 (+strand)-CMVe-CBAp-hRPE65-hBGt (304) prepared in the first step to produce single stranded DNA (ssDNA) for two reactions. In the first reaction, the PHAGEMID: M13mp19 (+strand)-CMVe-CBAp-hRPE65-hBGt (304) is prepared for use as the ssDNA PCR template: phage M13mp19 (−strand)-CMVe-CBAp-hRPE65-hBGt (306) to receive the PCR long primer by infecting an *E. coli* with *F. pilus* to make the ssDNA phage genome containing the negative-stranded cassette insert with single strand M13 rolling circle DNA and making supernatants to purify the positive strand. In the second reaction, pM13mp19 (+strand)-CMVe-CBAp-hRPE65-hBGt (304) is used to PCR amplify the plasmid backbone to generate a dsDNA vector backbone without the insert, generating the dsDNA linear PCR product M13mp19 backbone no insert (307), which will allow a very long priming positive strand representing the plasmid backbone for the pM13mp19 (−strand)-CMVe-CBAp-hRPE65-hBGt dsDNA plasmid (306).

The two resulting products, M13mp19 backbone no insert (307) and the antisense payload in positive M13 packaged strand (306), along with addition of ssDNA ITR extension oligonucleotides (308), are all mixed, heated to denature, and annealed; the newly formed Hind3 site is cut to linearize the hybrid template. The resulting linearized moiety is then annealed to the primer, and the forced PCR reaction occurs (309); it expresses only the single strand positive transgene expression cassette with self-formed functional ITR ends form a [ITR-cargo-ITR] amplicon template. The [ITR-cargo-ITR] template using the reverse primer will allow forced asymmetric amplification of the [ITR-cargo-ITR] template, giving rise only to the positive strand [ITR-cargo-ITR] amplicons (310). When transfected, this specialized ssDNA [ITR-cargo-ITR] amplicon AAV template (310), denoted ssAVV2DNA: IVT-CMVe-CBAp-hRPE65-hBGt-IVT in FIG. 4, will give rise to only positive ssDNA strand containing rAAV. The vector may be transfected as described herein into modified HEK293 cells or other packaging cell lines.

In another embodiment, rAAV vectors containing a single polarity genome may be produced via modification to the one or both ITR sequences. Modifications may include one or more base deletions or insertions. The [ITR-cargo-ITR] amplicon, with one or more modifications to its ITR regions can then be amplified via PCR as disclosed herein and used to produce rAAV vectors according to the method and system set forth herein. Due to the modification of the ITR sequence, single polarity rAAV vectors can be produced. Modification of the ITR sequence may occur within the A, B, C, or D elements of one or both ITRs of the [ITR-cargo-ITR] construct, or any combination thereof. The wild-type A, B, C, and D element sequences of the ITR are shown in FIG. 1. In an embodiment, the ITR DNA sequence is modified within the D element.

Having now generally described the invention, the same will be more readily understood through reference to the following examples, which are provided by way of illustration, and are not intended to be limiting of the disclosed invention, unless specified.

EXAMPLES

Example 1—High Efficiency and High Fidelity PCR Amplifications from a Plasmid Containing an [ITR-Cargo-ITR] Construct A commercially sourced GFP plasmid containing a cargo (transgene) expression cassette for EGFP, flanked by two ITR regions (part #: AAV-400, Cell Biolab Inc., San Diego, CA) (shown in FIG. 2) was used as a PCR template for a [ITR-cargo-ITR] construct (wherein the cargo is EGFP) and was subject to several PCR amplifications as follows:

Amplification #1

For PCR amplification #1, the following primer set was utilized:

Forward primer (AAV-GFP-F):

(SEQ ID NO: 1)
5'CTTTTGCTGGCCTTTTGCTCACATGTCCTGC3'

Reverse primer (AAV-GFP-R):

(SEQ ID NO: 2)
5' GTAAGGAGAAAATACCGCATCAGGCGCCCC3'

The PCR amplification reaction was carried out in 100 μL volume utilizing the following PCR reaction composition.

| Composition | Final Concentration | Volume (μL) |
|---|---|---|
| PCR water | — | 39.5 |
| Q5 5X buffer | 1X | 20 |
| 5X GC enhancer | 1X | 20 |
| dNTP 40 mM | 0.8 mM | 2 |
| Q5 Polymerase 2 U/ul | 0.02 U/uL | 1 |
| AAV-GFP-F | 0.5 uM | 0.5 |
| AAV-GFP-R | 0.5 uM | 0.5 |
| AAV-400-GFP plasmid | 1 ng/25 uL | 4 |
| 4M betaine | 0.5M | 12.5 |
| Total volume | | 100 |

The PCR reaction composition above was subjected to the below two-step PCR cycling parameters.

PCR Cycling Parameters

|  | Initial Denature 98° C. | Denature 98° C. | Annealing/ Extension 72° C. | Final Extension 72° C. |
|---|---|---|---|---|
| Duration | 30 se. | 10 sec. | 3 min. | 2 sec. |
| Cycles | 1 |  | 28 | 1 |

Figure 5:
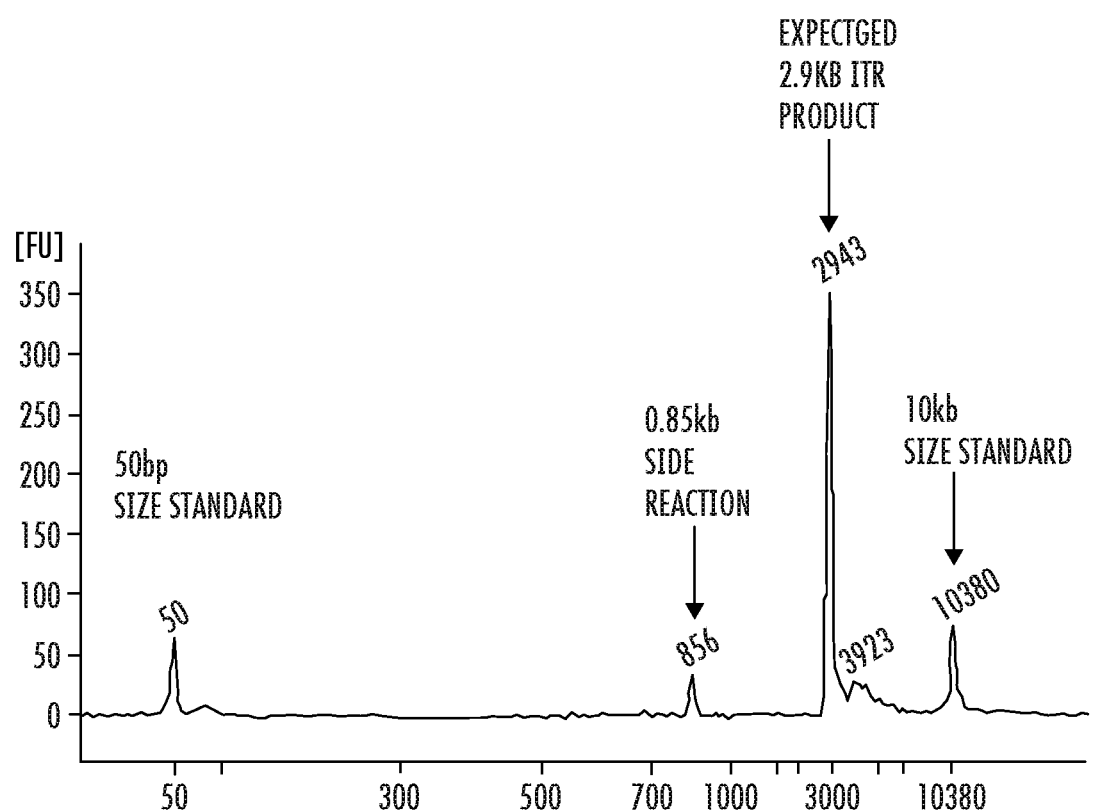
FIG. 5 is an electropherogram showing DNA amplicon characteristics as produced according to an embodiment of the invention.

As shown in FIG. 5, the resultant [ITR-EGFP-ITR] amplicon produced by the above described PCR reaction was detected via electropherogram obtained via an Agilent Bioanalyzer. As shown below, a large amount of [ITR-EGFP-ITR] amplicon was detected with minimal side reactions.

Amplification #2

Figure 2:
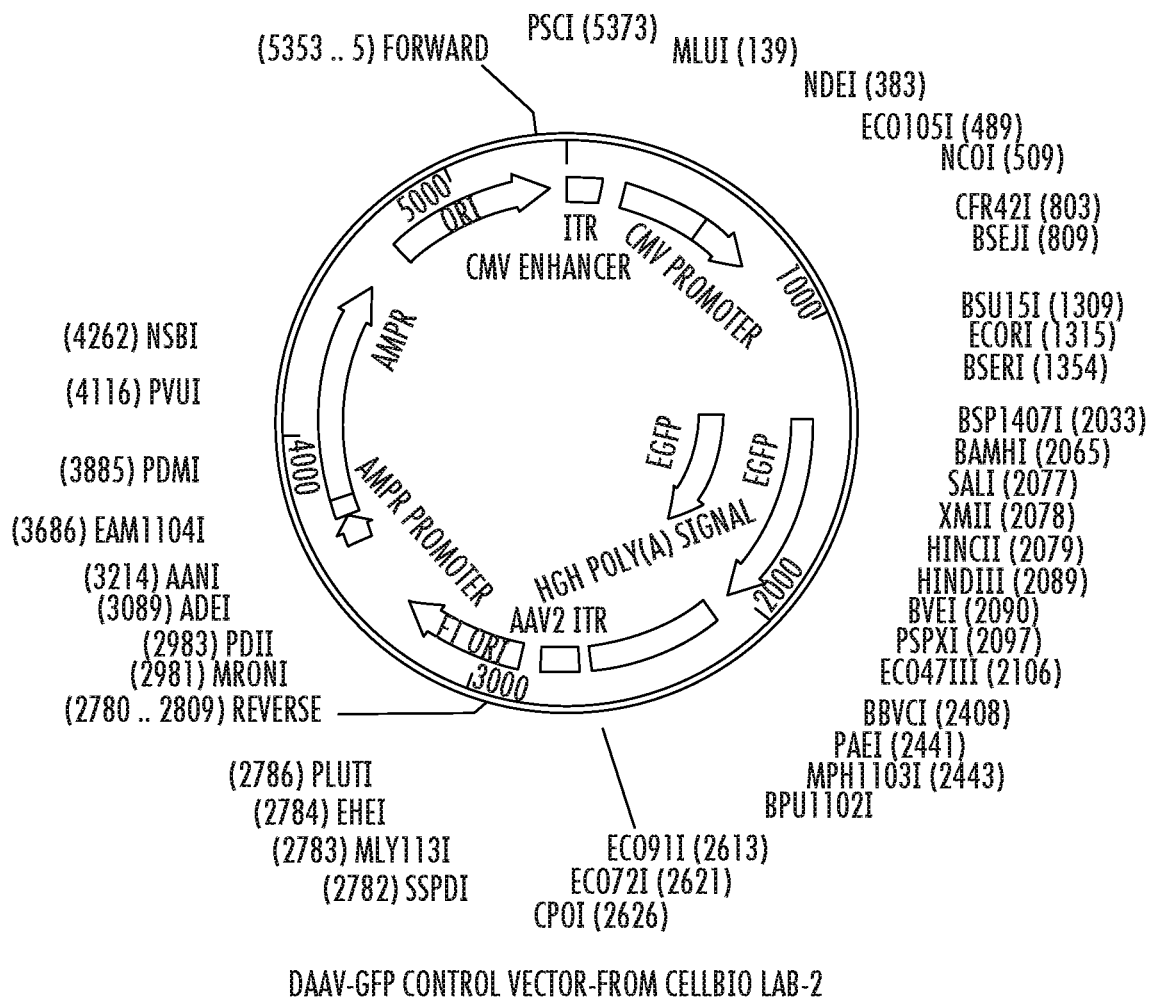
FIG. 2 is a plasmid map of a template [ITR-GFP-ITR] showing primer locations according to an embodiment of the invention.

For amplification #2, the same commercially sourced plasmid (see. FIG. 2) containing the [ITR-EGFP-ITR] construct from amplification #1 was used again as a template for PCR amplification of the [ITR-EGFP-ITR] construct. The PCR cycling parameters were identical to amplification #1, but the inclusion of betaine as part of the PCR reaction composition was removed.

Figure 6:
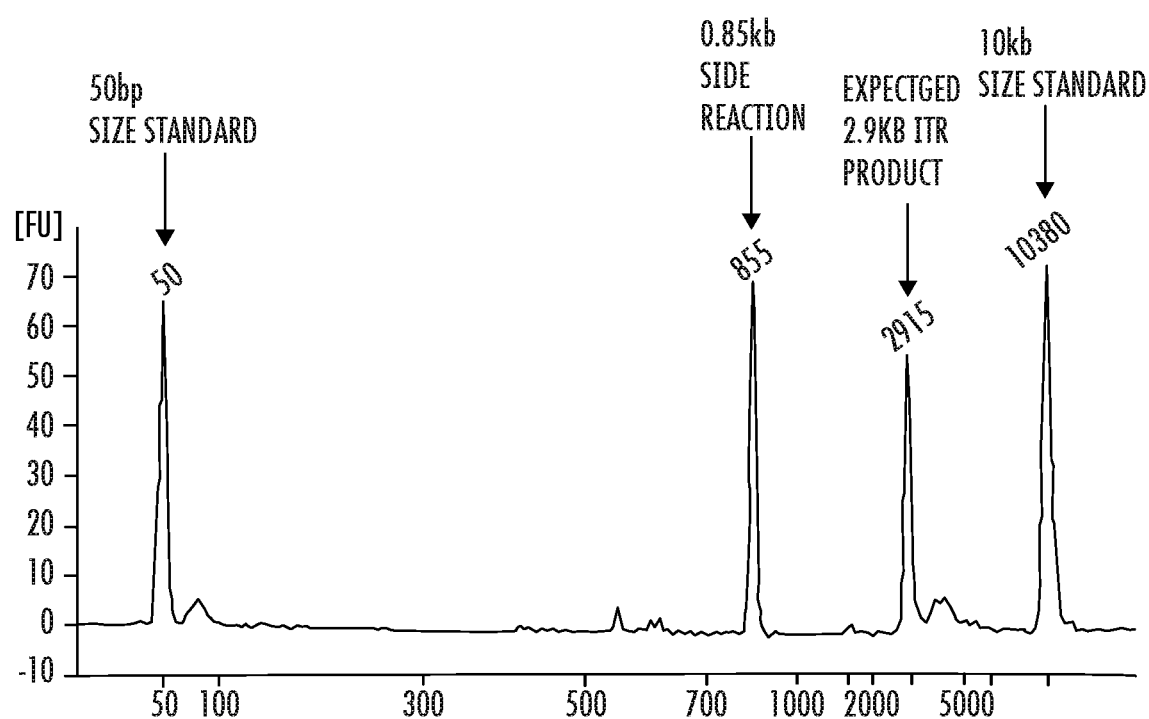
FIG. 6 is an electropherogram showing DNA amplicon characteristics as produced according to an embodiment of the invention.

As can be seen in FIG. 6, an electropherogram obtained via an Agilent Bioanalyzer, the removal of betaine from the PCR reaction composition greatly reduced the yield of the target [ITR-EGFP-ITR] construct and significantly increased side reactions as compared to the amplicon produced by amplification #1.

Amplification #3

For amplification #3, the same commercially sourced plasmid (see. FIG. 2) containing the [ITR-EGFP-ITR] construct used in amplification #1 was again used as a PCR template. The PCR cycling parameters were identical to amplification #1, but the betaine in the PCR reaction composition was replaced with 5% DMSO (another osmolyte).

Figure 7:
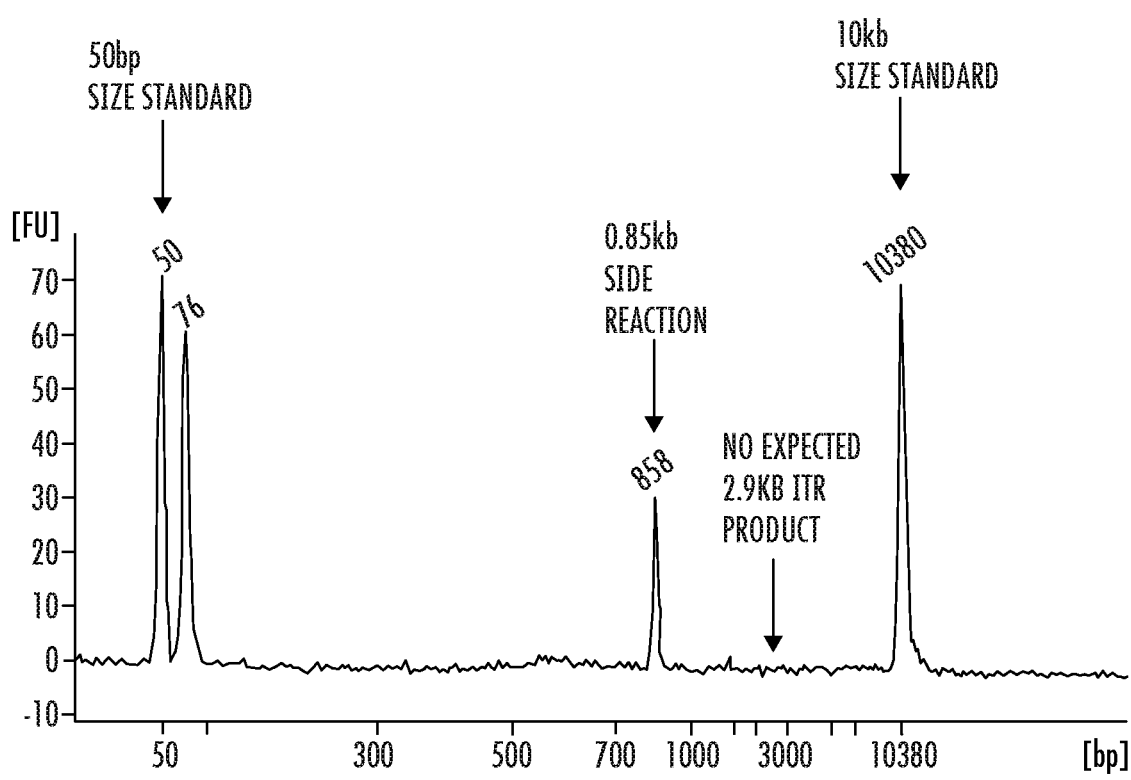
FIG. 7 is an electropherogram showing DNA amplicon characteristics as produced according to an embodiment of the invention.

As can be seen in FIG. 7, an electropherogram obtained via an Agilent Bioanalyzer, the substitution of 5% DMSO for betaine in the PCR reaction composition resulted in the failure of [ITR-EGFP-ITR] construct to amplify and also resulted in several undesirable side reactions.

Amplification #4

A fourth PCR amplification was conducted, again using the same commercially sourced plasmid used in amplification #1 as the [ITR-EGFP-ITR] PCR template. The forward and reverse primers used were as follows:

```
Forward primer:
                                  (SEQ ID NO: 3)
5' TCCTGGCCTTTTGCTGGCCTTTTGCTCACATGTCCTG3'

Reverse primer:
                                  (SEQ ID NO: 2)
5 'GTAAGGAGAAAATACCGCATCAGGCGCCCC3'
```

The PCR reaction composition was identical to amplification #1, but 0.75M betaine was used versus the 0.5M betaine used in amplification #1. In addition, the PCR cycling parameters from amplification #1 were adjusted to include a 5 minute annealing/extension time at 72° C.

Figure 8:
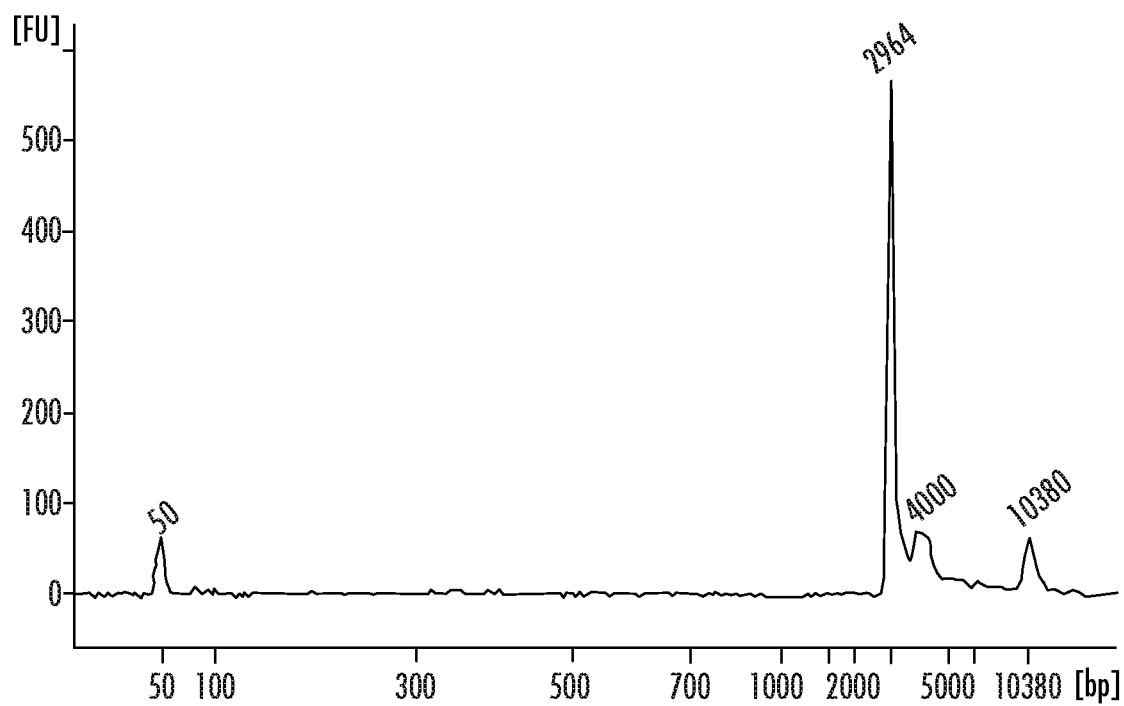
FIG. 8 is an electropherogram showing DNA amplicon characteristics as produced according to an embodiment of the invention.

As seen in FIG. 8, another electropherogram obtained via an Agilent Bioanalyzer, these modifications resulted in increased yield of the target [ITR-EGFP-ITR] construct and further reduced undesirable side reactions, resulting in a high-yield high-fidelity [ITR-EGFP-ITR] amplicon.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention.

Although the invention has been described with reference to the above examples and embodiments, it is not intended that such references be constructed as limitations upon the scope of this invention except as set forth in the following claims.

What is claimed is:

1. A method of manufacturing amplicon polynucleotides containing the sequence motif [ITR-cargo-ITR] via the polymerase chain reaction (PCR), said method comprising:
performing a PCR amplification reaction on a desired template DNA sequence containing a [ITR-cargo-ITR] DNA sequence motif, wherein the ITR is the wild type AAV ITR,
wherein the PCR amplification reaction uses a PCR primer pair such that the 3' terminus of both the forward and reverse PCR primers overlap only about the last 2-8 bases of the A/A' ITR sequences and the 5' terminus of both the forward and reverse PCR primers extend into about 20-35 bases of the flanking sequences,
wherein PCR cycling parameters comprise a combined annealing/extension step at a temperature greater than 70° C.,
wherein the PCR amplification reaction contains one or more osmolytes, wherein an osmolyte is betaine at a concentration of between 0.01 and 1M,
wherein the placement of the primers, the combined annealing/extension step, and betaine destabilize the ITR fold,
thereby producing a plurality of amplicon polynucleotides containing the desired [ITR-cargo-ITR] DNA sequence motif.

2. The method of claim 1, wherein the flanking regions have been designed for high-affinity PCR primer binding.

3. The method of claim 1, wherein the concentration of betaine used in the PCR amplification reaction is between 0.5 and 0.75M.

4. The method of claim 1 wherein the [ITR-cargo-ITR] sequence is derived from a plasmid.

5. The method of claim 1 wherein the [ITR-cargo-ITR] sequence is not derived from a plasmid.

6. The method of claim 1 wherein PCR cycling parameters further comprises an additional annealing/extension time at a temperature greater than 70° C. for a duration longer than 3 minutes.

7. A method of manufacturing sequence verified amplicon polynucleotides containing the DNA sequence motif [ITR-cargo-ITR] via the polymerase chain reaction (PCR), said method comprising:
performing a PCR amplification reaction on a desired template DNA sequence containing a [ITR-cargo-ITR] DNA sequence motif, wherein the ITR is the wild type AAV ITR,
wherein the PCR amplification reaction uses a PCR primer pair such that the 3' terminus of both the forward and reverse PCR primers overlap only about the last 2-8 bases of the A/A' ITR sequences and the 5' terminus of both the forward and reverse PCR primers extend into about 20-35 bases of the flanking sequences,
wherein PCR cycling parameters comprise a combined annealing/extension step at a temperature greater than 70° C., wherein the PCR amplification reaction contains one or more osmolytes, wherein an osmolyte is betaine at a concentration of between 0.01 and 1M, wherein the placement of the primers, the combined annealing/extension step, and betaine destabilize the ITR fold;
producing a plurality of amplicon polynucleotides containing the desired [ITR-cargo-ITR] DNA sequence motif;
pooling a representative sample of said amplicon polynucleotides containing the desired [ITR-cargo-ITR] DNA sequence motif; and
subjecting said pool representative sample of said amplicon polynucleotides containing the desired [ITR-cargo-ITR] DNA sequence motif to next generation sequencing (NGS).

8. The method of claim 7, wherein the concentration of betaine used in the PCR amplification reaction is between 0.5 and 0.75M.

9. The method according to claim 1, wherein the ITR is the wild type AAV ITR (SEQ ID NO: 4).

10. The method according to claim 1, wherein the 3' terminus of both the forward and reverse PCR primers overlap only the last 2 bases of the A/A' ITR sequences.

11. The method according to claim 7, wherein the ITR is the wild type AAV ITR (SEQ ID NO: 4).

12. The method according to claim 7, wherein the 3' terminus of both the forward and reverse PCR primers overlap only the last 2 bases of the A/A' ITR sequences.

* * * * *